United States Patent
Law

(12) 
(10) Patent No.: US 6,232,505 B1
(45) Date of Patent: May 15, 2001

(54) METHOXYACETONE PREPARATION

(75) Inventor: Michael P. Law, West Chester, PA (US)

(73) Assignee: ACRO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/519,398

(22) Filed: Mar. 3, 2000

(51) Int. Cl.[7] .................................................. C07C 45/37
(52) U.S. Cl. ................................... 568/385; 568/383
(58) Field of Search .................................. 568/382, 383, 568/385, 403

(56) References Cited

U.S. PATENT DOCUMENTS

| | | | |
|---|---|---|---|
| 3,462,495 | 8/1969 | Friedli | 260/590 |
| 4,141,919 | 2/1979 | Gremmelmaier | 260/594 |
| 4,218,401 | 8/1980 | Wymore | 567/402 |
| 4,233,246 | 11/1980 | Dudeck et al. | 568/402 |
| 4,480,135 | 10/1984 | Esposito et al. | 568/385 |
| 4,666,502 | 5/1987 | Seckinger et al. | 71/90 |
| 4,754,073 | 6/1988 | Venturello et al. | 568/311 |
| 5,576,188 | 11/1996 | Schlaeppi et al. | 435/7.93 |

OTHER PUBLICATIONS

CA:117:236226 abs of Appl Catal A 86(2) pp 147–63 by Mallat, 1992.*
CA:118:101518 abs of CS 274951, Dec. 1991.*
CA:121:34457 abs of Adv Catal Des., Proc Workshop, 2nd pp 53–72 by Strukul, 1992.*
G. Strukul, *Adv. Catal. Des., Proc. Workshop*, 2nd (1993) 53.
R. Zennaro et al., *J. Mol. Catal. 50* (1991) 269.
T. Mallat et al., *J. Catal. 142* (1993) 237.
T. Mallat and A. Baiker, *Appl. Catal. A 79* (1991) 41.
T. Mallat and A. Baiker, *Appl. Catal. A 86* (1992) 147.
A. L. Miller et al., *J. Am. Chem. Soc. 71* (1949) 3559.
K. Heyns and M. Paulsen, *Angew. Chem. 69* (1957) 600.
O. Bortolini et al., *J. Org. Chem. 51* (1986) 2661.
G. Barak et al., *J. Org. Chem. 53* (1988) 3553.

* cited by examiner

Primary Examiner—Jean F. Vollano
(74) Attorney, Agent, or Firm—Jonathan L. Schuchardt

(57) ABSTRACT

A process for making methoxyacetone is disclosed. The process comprises oxidizing 1-methoxy-2-propanol in the liquid phase using aqueous hydrogen peroxide and a Group 8–10 transition metal catalyst. The process gives high alcohol conversions (>95%) and good selectivities (>80%) to methoxyacetone using mild conditions, simple equipment, and readily available reagents.

11 Claims, No Drawings

METHOXYACETONE PREPARATION

FIELD OF THE INVENTION

The invention relates to the preparation of methoxyacetone. In particular, the invention involves liquid-phase oxidation of 1-methoxy-2-propanol (i.e., propylene glycol methyl ether) to methoxyacetone using hydrogen peroxide and a transition metal catalyst.

BACKGROUND OF THE INVENTION

Methoxyacetone (1-methoxy-2-propanone) provides a key structural piece in the synthetic route to metolachlor and other herbicidal compositions (see, e.g., U.S. Pat. Nos. 4,666,502 and 5,576,188). In addition, methoxyacetone has been used as a polar organic solvent, a chemical intermediate, a Schiff base reagent, an additive for cement compositions, and as an aid in the cryogenic preservation of organs.

Catalytic dehydrogenation of 1-methoxy-2-propanol (propylene glycol methyl ether) is one approach to methoxyacetone. This is generally a vapor-phase process in which the alcohol and air are fed into a hot, tubular reactor that contains a catalyst. For example, U.S. Pat. No. 3,462,495 teaches to use a "calcium nickel phosphate" catalyst and air at 425° C. to convert 1-methoxy-2-propanol to methoxyacetone. Similarly, U.S. Pat. No. 4,233,246 uses air and a silver/copper catalyst at 450–700° C. to effect the oxidation. U.S. Pat. No. 4,218,401 describes another vapor-phase oxidation at 225–600° C. using air and a supported Group 8–10 transition metal catalyst. Copper chromite (see U.S. Pat. No. 4,141,919) has also been used as a catalyst. Unfortunately, the yield and selectivity from these catalytic dehydrogenation processes is often less than desirable.

Liquid-phase processes are also known. Chromic acid (sulfuric acid+sodium dichromate) will oxidize 1-methoxy-2-propanol (see *J. Am. Chem. Soc.* 71 (1949) 3558), but the yield of methoxyacetone is generally less than 30%. Mallat et al. have described liquid-phase oxidation of 1-methoxy-2-propanol using promoted, supported platinum catalysts and air as an oxidant (see, e.g., *J. Catal.* 142 (1993) 237 or *Appl. Catal.* A 79 (1991) 41.) Much earlier, Heyns and coworkers often used liquid-phase catalytic oxidation with air or oxygen and platinum on carbon to selectively oxidize secondary alcohols to ketones under mild conditions in the synthesis of carbohydrates (*Angew. Chem.* 69 (1957) 600).

Unfortunately, liquid-phase oxidation of 1-methoxy-2-propanol using air and a transition metal catalyst as suggested above can be challenging to practice. In our labs and under a variety of reaction conditions, including ones similar to those suggested earlier (Pt/C catalyst, atmospheric pressure, 60° C., aqueous solution), we obtained less than 2% yields of methoxyacetone (see Comparative Example 3 below). Similar results were observed for air oxidations at high pressure (1000 psi) as shown by Comparative Example 4.

Hydrogen peroxide has been used in a number of liquid-phase oxidation processes. For example, U.S. Pat. No. 4,480,135 teaches that secondary alcohols can be oxidized to ketones using aqueous hydrogen peroxide and a synthetic zeolite containing titanium. Hydrogen peroxide has also been used with a phosphotungstate in a two-phase system (see U.S. Pat. No. 4,754,073). The organic phase contains the secondary alcohol and tungstate, while the aqueous phase contains $H_2O_2$. Hydrogen peroxide has apparently not been used to make methoxyacetone.

In sum, an improved process for making methoxyacetone is needed. Preferably, the process could be practiced using common laboratory equipment under mild conditions with readily available reagents. A valuable process would improve on the yield and selectivity of methoxyacetone compared with that available from known vapor and liquid-phase oxidation processes.

SUMMARY OF THE INVENTION

The invention is a process for making methoxyacetone. The process comprises oxidizing 1-methoxy-2-propanol in the liquid phase using aqueous hydrogen peroxide and a Group 8–10 transition metal catalyst. I surprisingly found that high alcohol conversions (>95%) and good selectivities (>80%) to methoxyacetone are achieved under mild conditions with simple equipment and readily available reagents.

DETAILED DESCRIPTION OF THE INVENTION

The invention is a process for converting 1-methoxy-2-propanol (also known as propylene glycol monomethyl ether or propylene glycol methyl ether) to methoxyacetone (1-methoxy-2-propanone).

The process is performed in the liquid phase. By "liquid phase" we mean that the reaction mixture is mostly in liquid rather than gaseous form. Normally, the process is performed at or below the boiling point of the reaction mixture. It is possible, however, to perform the process at greater than atmospheric pressure and above the boiling point of the reaction mixture. Preferably, however, the process is performed at or slightly above atmospheric pressure. In contrast, most of the reported preparations of methoxyacetone are vapor-phase processes that are performed at temperatures well above the boiling point of the reaction mixture and/or at pressures much greater than atmospheric.

Hydrogen peroxide is used as the source of oxygen. While any desired source of hydrogen peroxide can be used, I found that commercially available 30% aqueous $H_2O_2$ is well-suited for use in the process. Higher concentrations (e.g., 50%) of hydrogen peroxide are also suitable and are available commercially, but these are less preferred because they require more care to handle safely. Lower concentrations (e.g., 3%) are also suitable. The amount of hydrogen peroxide needed will depend on a number of factors, including the reaction temperature, the concentration of mixture, the rate of addition of the hydrogen peroxide, and other factors. Generally, an excess of hydrogen peroxide is used. Preferably, the amount will be within the range of about 1 to about 100 moles of $H_2O_2$ per mole of 1-methoxy-2-propanol. A more preferred range is from about 2 to about 50 moles of $H_2O_2$ per mole of the alcohol; most preferred is the range from about 10 to about 30 moles per mole.

Interestingly, air is not a suitable oxidant. As Comparative Example 3 shows, sparging air through the reaction mixture at 200 mL/min. gives less than 2% yield of methoxyacetone. Conversion to methoxyacetone remains negligible even when air is used under a pressure of 1000 psi (see Comparative Example 4).

A Group 8–10 transition metal catalyst is used in the process. Suitable catalysts include a metal selected from iron, ruthenium, osmium, cobalt, rhodium, iridium, nickel, palladium, and platinum. Catalysts that contain a Group 10 metal are preferred; platinum and ruthenium are particularly preferred. Any convenient source of the transition metal can be used. Generally, it is preferred to use a finely divided metal that has been deposited on a support such as activated carbon, silica, alumina, or calcium carbonate. Many of these catalysts are commercially available. Examples include platinum on activated carbon, platinum on alumina, palladium on activated carbon, rhodium on carbon, ruthenium on carbon, and the like.

The amount of Group 8–10 transition metal catalyst used depends on the particular catalyst used, the reaction conditions, and other factors. Generally, the amount will be within the range of about 0.00001 to about 0.1 mole of transition metal per mole of 1-methoxy-2-propanol. A more preferred range is from about 0.01 to about 0.0001 moles per mole.

The process can be performed over a wide temperature range. Preferably, the process is performed at a temperature within the range of about 0° C. to about 100° C., more preferably from about 40° C. to about 95° C., and most preferably from about 60° C. to about 90° C.

The process is normally performed in aqueous media. The concentration of 1-methoxy-2-propanol available for reaction is conveniently adjusted by diluting it with water, preferably to provide a solution containing from about 5 to about 80 wt. %, more preferably from about 10 to about 50 wt. % of 1-methoxy-2-propanol. In one convenient procedure, all of the Group 8–10 transition metal catalyst is added to the aqueous 1-methoxy-2-propanol mixture, which is heated to the desired reaction temperature. Hydrogen peroxide is then added gradually to the well-agitated mixture and the reaction progress is monitored by gas-liquid chromatography.

A weak base can be included in the reaction mixture, if desired, to keep the pH of the mixture at or above 7. This will minimize the risk of acid-catalyzed side-reactions such as catalyst poisoning or aldol condensations. Suitable weak bases include sodium carbonate, sodium bicarbonate, potassium dihydrogen phosphate, and the like.

The following examples merely illustrate the invention. Those skilled in the art will recognize many variations that are within the spirit of the invention and scope of the claims.

EXAMPLE 1

Preparation of Methoxyacetone

A 500-mL, three-neck flask equipped with chilled (0° C.) condenser, stirring bar, thermometer, and addition funnel is charged with aqueous 1-methoxy-2-propanol (50 g of 20 wt. % solution). The flask is immersed in a constant-temperature bath on a programmable hot plate/stirrer set for 80° C. and 800 rpm. Hydrogen peroxide (250 mL of 30% $H_2O_2$ solution) is charged to the addition funnel. The catalyst, 10% platinum on activated carbon (1.326 g, 1 mole of Pt per 250 moles of 1-methoxy-2-propanol), is added to the flask, along with sodium bicarbonate (1.30 g). The hydrogen peroxide solution is then added slowly over 4 h at 80° C. Analysis of the reaction mixture by gas-liquid chromatography (GLC) using 1,4-dioxane as a reference standard indicates >95% conversion of 1-methoxy-2-propanol and about 84% selectivity to methoxyacetone.

EXAMPLE 2

Preparation of Methoxyacetone

The apparatus of Example 1 is modified by replacing the addition funnel with a plastic syringe and 12"needle. The syringe is mounted on a Sage Instruments Model 341B syringe pump. The flask is charged with aqueous 1-methoxy-2-propanol (125 g of 20 wt. % solution). The catalyst is 10% platinum on activated carbon (3.79 g). No sodium bicarbonate is used. Hydrogen peroxide (87 g of 30% $H_2O_2$ solution) is added slowly from the syringe over 4 h at 80° C. Analysis of the reaction mixture by GLC indicates >95% conversion of 1-methoxy-2-propanol and about 94% selectivity to methoxyacetone.

Comparative Example 3

Attempted Preparation of Methoxyacetone Using Air as the Oxidant

Many attempts are made to convert 1-methoxy-2-propanol to methoxyacetone using platinum or palladium on carbon using air as the oxidant at atmospheric pressure. Different sources of catalysts are tried. The concentration of 1-methoxy-2-propanol is varied from 5% to 100%. Reactions are performed with and without sodium bicarbonate. Reaction temperatures of 40–80° C. are used. The air sparge rate is varied from 100 to 200 mL/min. In every case, very little conversion occurs, and the amount of methoxyacetone measured by GLC is always less than 1.5%.

In a typical example, a 500-mL, three-neck flask equipped with condenser, stirring bar, thermometer, and sparging tube is charged with aqueous 1-methoxy-2-propanol (300 g of 10 wt. % solution). The flask is immersed in a constant-temperature bath on a programmable hot plate/stirrer set for 60° C. and 800 rpm. The catalyst, 10% platinum on activated carbon (1.5 g), is added to the flask, along with sodium bicarbonate (1.5 g). Air is sparged through the reaction mixture at 100 mL/min. while the reaction mixture is heated for 3 h at 60° C. Analysis of the reaction mixture by GLC using 1,4-dioxane as a standard shows a yield of methoxyacetone of about 1.3%.

Comparative Example 4

Attempted Preparation of Methoxyacetone with Air and High Pressure

Many attempts are made to convert 1-methoxy-2-propanol to methoxyacetone using platinum or palladium on carbon using air as the oxidant at about 1000 psi. Reactions are performed with and without sodium bicarbonate. Reaction temperatures of 40–80° C. are used. In each case, very little conversion occurs, and the amount of methoxyacetone measured by GLC is always less than 1.5%.

In a typical example, a one-liter, stainless-steel autoclave reactor is scrupulously cleaned with nitric acid, multiple water rinses, and a final soak at 100° C. for 0.5 h with 1-methoxy-2-propanol. The clean, dry reactor is charged with aqueous 1-methoxy-2-propanol (300 g of 10 wt. % solution), 10% platinum on activated carbon (1.5 g), and sodium bicarbonate (1.5 g). The reactor is pressurized to 1000 psi with air, and the stirred mixture is heated to 60° C. for 2.5 h. Analysis of the reaction mixture by GLC using 1,4-dioxane as a standard shows a yield of methoxyacetone of about 1.4%.

The preceding examples are meant only as illustrations. The following claims define the invention.

I claim:

1. A process which comprises oxidizing 1-methoxy-2-propanol in the liquid phase using aqueous hydrogen peroxide and, as a catalyst, finely divided platinum or ruthenium deposited on a support selected from the group consisting of activated carbon, silica, alumina, and calcium carbonate to produce methoxyacetone.

2. The process of claim 1 wherein the catalyst is platinum on activated carbon.

3. The process of claim 1 performed at a temperature within the range of about 0° C. to about 100° C.

4. The process of claim 1 performed at a temperature within the range of about 60° C. to about 90° C.

5. The process of claim 1 wherein the conversion of 1-methoxy-2-propanol exceeds 90%.

6. The process of claim 1 wherein the selectivity to methoxyacetone exceeds 80%.

7. The process of claim 1 wherein the selectivity to methoxyacetone exceeds 90%.

8. A process which comprises oxidizing 1-methoxy-2-propanol in the liquid phase at a temperature within the range of about 60° C. to about 90° C. using aqueous hydrogen peroxide and platinum on activated carbon to produce methoxyacetone.

9. The process of claim 8 wherein the conversion of 1-methoxy-2-propanol exceeds 90%.

10. The process of claim 8 wherein the selectivity to methoxyacetone exceeds 80%.

11. The process of claim 8 wherein the selectivity to methoxyacetone exceeds 90%.

* * * * *